(12) United States Patent
Kippeny

(10) Patent No.: US 8,365,575 B2
(45) Date of Patent: Feb. 5, 2013

(54) CHEMICALLY MODIFIED ORGANIC CDC BASED RAPID ANALYSIS SYSTEM

(75) Inventor: Tadd C. Kippeny, Mt. Airy, MD (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 544 days.

(21) Appl. No.: 12/611,663

(22) Filed: Nov. 3, 2009

(65) Prior Publication Data

US 2010/0107731 A1    May 6, 2010

Related U.S. Application Data

(60) Provisional application No. 61/198,678, filed on Nov. 6, 2008.

(51) Int. Cl.
*G01N 30/04*    (2006.01)
(52) U.S. Cl. .................... 73/23.41; 73/23.37
(58) Field of Classification Search ............. 73/23.41, 73/23.37
See application file for complete search history.

(56) References Cited

U.S. PATENT DOCUMENTS

| | | | | |
|---|---|---|---|---|
| 5,313,061 A | * | 5/1994 | Drew et al. | 250/281 |
| 5,528,032 A | * | 6/1996 | Uchiyama | 250/288 |
| 6,272,937 B1 | * | 8/2001 | Mengel et al. | 73/863.21 |
| 7,841,244 B2 | * | 11/2010 | Barket et al. | 73/862.21 |
| 2006/0165584 A1 | * | 7/2006 | Gogotsi et al. | 423/445 B |

OTHER PUBLICATIONS

International Search Report and the Written Opinion of the International Searching Authority issued in corresponding PCT/US 09/63399 dated Dec. 31, 2009.

\* cited by examiner

*Primary Examiner* — Hezron E Williams
*Assistant Examiner* — Paul West
(74) *Attorney, Agent, or Firm* — Rossi, Kimms & McDowell; Marc A. Rossi; Daniel J. Long

(57) ABSTRACT

A method of performing chemical analysis is disclosed. The method includes the steps of forming carbide-derived carbon (CDC) material having a plurality of pore size, surface chemistry, and surface electrical properties. An array of the surface functionalized CDCs are used for atmospheric sampling, in which chemicals in the atmosphere are adsorbed on the CDCs. The adsorbed samples are desorbed later for analysis by a plurality of individual mass spectrometers.

24 Claims, 10 Drawing Sheets

CHEMICALLY MODIFIED ORGANIC CDC BASED RAPID ANALYSIS SYSTEM

This application is based on and claims priority to U.S. Provisional Patent Application 61/198,678, filed on Nov. 6, 2008. The disclosure of the priority application in its entirety, including the drawings, claims, and the specification thereof, is incorporated herein by reference. In addition, the contents of all other documents referenced herein are incorporated by reference in their entirety.

BACKGROUND OF THE INVENTION

A. Field of the Invention

The present invention relates to methods and apparatus for chemical analysis and more particularly to deployable chemical air sampling systems.

B. Description of the Related Art

Current techniques for chemical air sampling typically use zeolites or metal organic frameworks (MOFs). Zeolites and MOFs derive pore size from their structure, and pore size is "tuned" in fixed size steps. Changing pore size requires a compositional change which is achieved by a chemical change of the linking unit, so that a change in pore size is tied inextricably to the chemical interactivity of pore lining, i.e., a specific chemical lining is linked to given pore size regime. Because of this, it is impossible, for example, to create MOFs with 1 nm and 10 nm pore sizes which have the exact same chemical lining.

In order to selectively sample a wide variety of chemical analytes that differ in size, shape, hydrophilicity, etc., techniques have been employed in which a mixture of adsorbents is used. However, heterogeneous mixtures introduce challenging desorption conditions due to the unique behavior of each component.

The need for environmental monitoring of toxic gases has increased dramatically in recent years for defense, homeland security, and industrial applications. The need exists for a deployable chemical air sampling system in which pore size is not linked to chemical interactivity of the pore lining. The system should be versatile, rapid, and yet low cost. The present invention is directed to meeting this need.

SUMMARY OF THE INVENTION

An air sampling assembly is provided according to the invention which comprises a plurality of sampling coupons, each sampling coupon comprising a plurality of different carbide-derived carbon (CDC) variants which vary with respect to one or more of pore size, surface chemistry, and surface electrical properties, for adsorbing chemicals in an air sample; and an indexable container for holding said plurality of sampling coupons, which allows the sampling coupons to be individually addressed. The air sampling assembly additionally may comprise means for indexing the indexable container, such as a stepper motor. The air sampling assembly additionally may comprise means for desorbing the chemicals which are adsorbed on the sampling coupons, and the desorbing means can comprise IR heating. The air sampling assembly additionally may comprise means for analyzing the chemicals which have been desorbed from the sampling coupons. The analyzing means may comprise a mass spectrometer, and also can additionally comprise a gas chromatograph. The air sampling assembly additionally may comprise means for identifying the chemicals which have been desorbed and analyzed, and the identifying means can comprise a mass spectrometry library. The air sampling assembly also may additionally comprise means for recording the time and location where the sample was collected. Each of the plurality of CDC variants is unique. A matrix of 8 unique CDC variants and a ninth control comprising all of the 8 unique CDC variants preferably are contained on each sampling coupon.

The invention also provides a method of air sampling, comprising providing an indexable container containing a plurality of sampling coupons, each sampling coupon comprising a plurality of different carbide-derived carbon (CDC) variants which vary with respect to one or more of pore size, surface chemistry, and surface electrical properties, for adsorbing chemicals in an air sample; and addressing one sampling coupon and exposing it to the air so that a chemical in the air is adsorbed on the plurality of CDC variants on the sampling coupon. The method additionally may comprise desorbing the chemicals which are adsorbed on the sampling coupons. The air sampling assembly additionally may comprise analyzing the chemicals which have been desorbed from the sampling coupons, as well as identifying the chemicals which have been desorbed and analyzed. The identifying may comprise chemo-informatics. The air sampling assembly additionally may comprise recording the time and location where the sample was adsorbed.

Compared to carbon nanotubes (CNT), zeolites, metal organic frameworks (MOF), mesoporous silica, activated carbon, composite materials, and organic polymer derived materials, CDC offers almost unlimited opportunities for porosity (size, shape, and surface chemistry) tuning, in combination with a high specific surface area (SSA) and a narrow pore size distribution. For example, CDC produced from $Ti_3SiC_2$ at moderate temperatures has a narrower pore-size distribution than single-wall carbon nanotubes or activated carbons and is comparable to that of zeolites. However, for a given zeolite structure, only a single discrete pore size is typically evident thus coupling of the pore size with SSA. Extreme fine tuning of CDC pore sizes, from 0.6 to 3 nm, is readily attainable at temperatures between 300 and 800° C. CDC pore size can be tuned continuously with a very high (sub-nanometer) precision, which is impossible in most other materials. Zeolites or MOFs, because the pore size is determined by the crystal structure do not have this capability. Narrow pore size distribution is much more important for CDC than order and has a much greater impact on adsorption/desorption rates and profiles. The ability to tune the pore size to perfectly fit the size and chemistry of the molecule of interest, and the availability of a large volume of pores with required size is of key importance, not the structure ordering or any other parameter. This independence leads to a high heat of adsorption, which provides not only catching and keeping the gas molecules, but also releasing them quickly for analysis.

In addition, initial surface chemistry of CDC can be maintained or covalently modified without changing the pore size (except for the size of the functional group). Again, this cannot be done in many other porous materials, such as nanotubes where tube sidewalls are very difficult to modify. Furthermore, a change in MOF pore size necessitates a change in the internal chemical composition. Therefore, the pore size in MOFs is limited by what this chemistry can deliver. It is impossible to make a MOF with 5 nm pores, which is a feat easily obtainable with CDC.

BRIEF DESCRIPTION OF THE DRAWINGS

The foregoing advantages and features of the invention will become apparent upon reference to the following detailed description and the accompanying drawings, of which.

DETAILED DESCRIPTION OF SPECIFIC EMBODIMENTS

Figure 1:
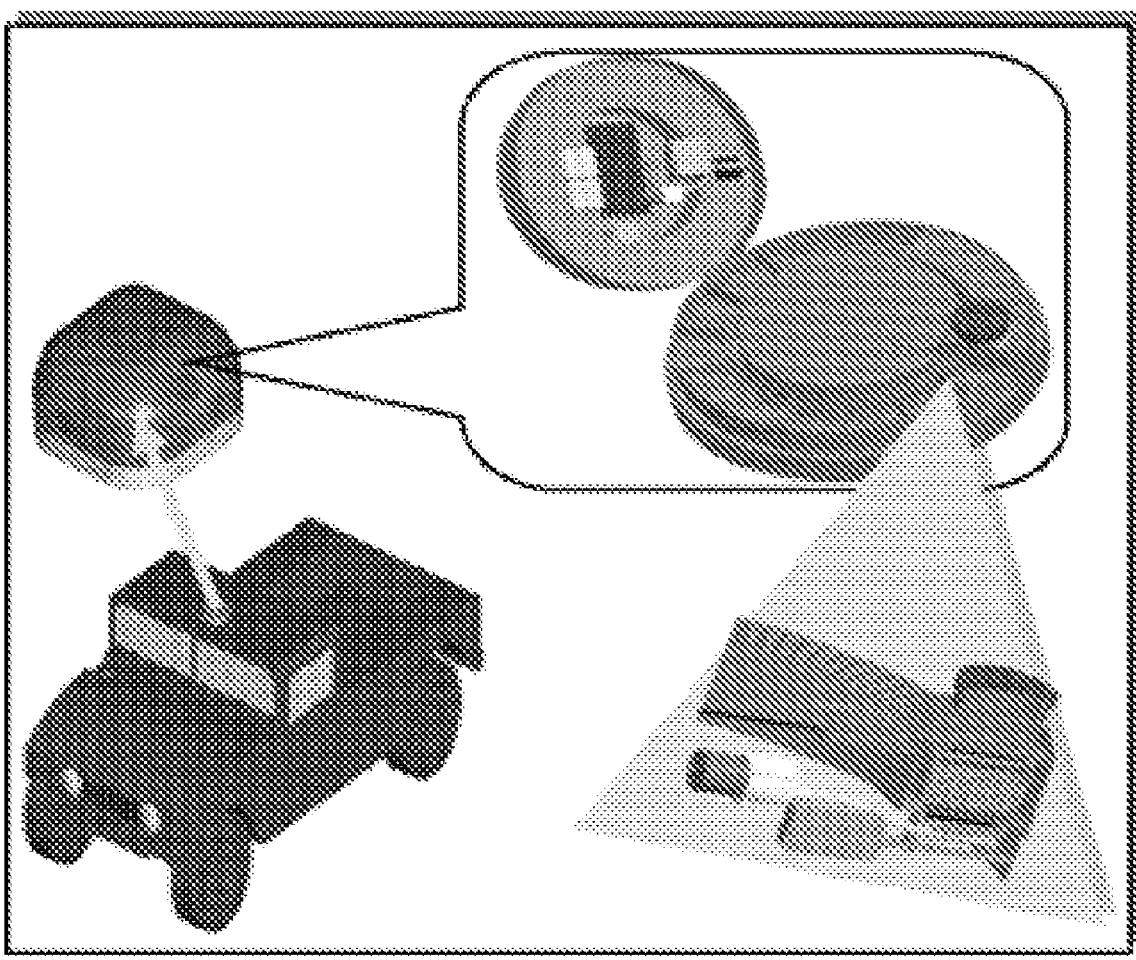
FIG. 1 is diagram of an integrated COBRA system, including indexed sampling carousel, 100 multi-channel coupons, battery, GPS, and pump.

The present invention uses Chemically Derived Carbon (CDC) as the basis for a chemical air sampling system. Unlike zeolites and MOFs, pore size in CDC is not linked to chemical structure. Thus, changing pore size in CDC does not require the expense of making a variety of structures, each of which includes a compositional change. Moreover, pore size in CDC is not tied to the chemical interactivity of pore lining, allowing a disconnect between pore sizing and functionalization. A CDC material with any pore size can be subjected to functionalization after it is made. This allows materials with various pore sizes to be made which have the exact same chemical lining. This unique advantage of CDC to functionalize after determining pore size allows for specific chemical design of a functionalized CDC towards both a distinct chemical compound (such as a chemical nerve agent) or a broad class of chemical compounds (such as aromatics).

Functionalized CDC allows for selective adsorption of differing chemical species while minimizing interactions with overwhelming atmospheric species such as oxygen, nitrogen, and water vapor. These atmospheric components typically overwhelm standard sorbent materials. For example, surface modification of CDC with a simple species such as ammonia significantly reduces the adsorption of water vapor (0.7% mass increase@ 90% relative humidity) compared to 15% for unfunctionalized CDC. In addition, typical adsorbent materials suffer from "bumping" in which a heavy molecular weight sample species drives off a lighter molecular weight species. Since CDC is tuned to a specific chemical class or even a specific molecule, bumping is greatly minimized. Thus, a heavy acid is not able to bump a lighter aliphatic compound, as these compounds would be preferentially bound on different CDCs (both pore size and surface lining).

CDC is formed by leaching metal(s) from metal carbide in a high temperature, halogenated environment. Since the metal carbide lattice is used as a template and metal is extracted layer-by-layer, atomic level control can be achieved in the synthesis process and the structure of the carbon can be templated by the carbide structure, with an opportunity for further structure modification by controlling the temperature, composition of the environment and other process variables. The result is a nanoporous carbon skeleton having nanometer-tunable pore sizes (0.6-3 nm) with a narrow size distribution. Pore size is a function of both the specific carbide initially chosen for processing, as well as the temperature of the processing. The choice of starting carbide and post processing temperature are the preferred parameters to be varied in tuning the pore size.

Some of the metal carbides, such as $Ti_3SiC_2$, are soft ceramics which can be machined into a variety of complex shapes and particle sizes, allowing for a wide range of forms. This polymorphic functionality is a great advantage of the CDC hyperadsorptive material and easily lends itself to many different applications and environments.

The CDC material can be further treated to have specific interactions(s) through attachment chemistry. Chemical coupling via carbon-carbon bond formation can be accomplished through one step gas treatments, electrochemical reduction of diazonium salts or multi-step carboxylate amidation. Functionalization of the internal pores with various "wetting agents" complements the native pore sizing with broad-class chemical interactions such as Van der Walls, dipole-dipole, or ionic forces.

The ability to alter the chemical nature of the pore by surface modification is a substantial benefit of using CDC hyperadsorptive material. Gas-treated functionalized CDC, in combination with pore size, differentiates among test molecules and greatly repels water vapor. Surface treatments can be performed with various methods, such as gas treatment, carboxylate amidation, and diazonium coupling. The smallest of CDC pores easily can be functionalized by a variety of gas streams. The treatment of the CDC material with aqueous nitric acid followed by thionyl chloride acetylates the carbon surface. Li, *Carbon* 2005, 43, 2883-2893. The carbonyl group is then susceptible to nucleophilic attack by amine-bearing wetting agents. The carboxylate amidation approach allows for a wide range of functional groups to be attached and does not require aromaticity; however, the end product is more susceptible to chemical reaction via amide hydrolysis. Finally, attachment of aromatic compounds (ArR) by electrochemical diazonium reduction creates highly variable functionality via a chemically inert carbon-carbon bond. Diazonium coupling, the preferred method, focuses on three classes of compounds based on the desired physiosorptive properties: (a) electrostatic (b) hydrophobic and (c) polar. Cyclic voltammetry is used determine the extent of functionalization. Yang, *Inorganic Chemistry Communications* 2005, 8, 853-857; Masheter, *Journal of Materials Chemistry* 2007, 17, 3008-3014.

CDC materials exhibit excellent adsorptive performance with respect to chemical agents that have no specific chemical interaction and must be captured purely by London forces. Therefore, CDC has been discovered to be an excellent adsorbent for the noble gases. Also, a potential can be applied across the CDC for trapping polarizable analytes, which allows selection between "hard" and "soft" electronic species, e.g., neon versus xenon.

Thus, CDC provides multiple orthogonal chemical selection criteria: molecular shape/size, chemical class, and polarizability. These variables can be independently adjusted by modification of the CDC pore size, internal chemical modification, and electrical properties. This allows, for example, a small, hard, positively charged amine species such as dimethylformamide, to be uniquely adsorbed as a class while excluding a small, soft, neutral species such as xenon. This type of exclusion is not possible with traditional atmospheric sampling materials.

CDC's ability to perform gas separation enables reversible binding to molecules of interest and a correlation concept that greatly reduces analysis time by reducing or eliminating the GC step in the analysis process, enabling direct injection into a mass spectrometer.

Synthesis of CDC is well characterized and has rapid manufacturing times. The low cost of starting carbides and a well known simple chlorination process means that the present invention provides a low cost alternative to existing technologies CDC offers the following unique features:

- Ability to change pore size to capture a wide variety of gas molecules through selective pore size and surface modification
- High adsorption capacity to capture more gas per unit volume
- Ability to engineer the pore size, shape, and order of the system to increase desorption rate
- Allows polymorphic packaging and desorption possibilities and increased adsorption and desorption rates
- Ability to exclude water In particular, the CDC pore surface can be uniquely modified to selectively adsorb desired gas molecules and minimize adsorption of undesirable, but ubiquitous, atmospheric species (water rejection). This is not the case for many of the competitive technologies. In addition, due to the high gas adsorption capacity of CDC from its high surface area and pore volume, only a single gram is required for a broad loading range of each analyte. One gram of CDC adsorbent costs only 9¢, including the cost of surface modification. Furthermore, while highly ordered pores typically are required for rapid controlled desorption, CDC does not follow this trend. Also, CDC can be easily fabricated into a variety of shapes, films, fibers, nano-tubes, powders, pellets, membranes and whisker, with or without mesopores, all with large surface areas of up to 2,200 $m^2/g$. This ability allows optimization of the adsorption and desorption rates and can minimize packaging requirements and cost.

Finally, water is a ubiquitous atmospheric contaminate which leads to many sampling problems. While unmodified CDC material adsorbs approximately 15% of its weight of water when exposed to humid air (unpublished data Y. Gogotsi), it has been found that chemical modification of CDC can greatly reduce water adsorption. For example, water adsorption isotherms show that a CDC material with a simple ammonia post treatment has the ability to exclude water as indicated by the less than 1% mass change in a 90% relative humidity atmosphere. Thus, with proper functionalization, water adsorption by CDC is greatly diminished, and often the same adsorbent features that enable hyperadsorptivity for certain compounds also enhance unwanted water adsorption.

The CDC material forms the basis for a chemically-modified organic CDC-based rapid analysis (COBRA). An array of CDC material containing various pore sizes, surface chemistry, and surface electric properties, enables orthogonal chemical selection criteria with the COBRA system, i.e., molecular shape/size, chemical class, and/or polarizability, and uses tuning in three dimensions to provide a versatile, rapid sampling array. With this selective array, desorption of the contents of each CDC derivative to an individual mass spectrometer, can provide unique identification of a chemical compound through the application of informatics techniques.

The COBRA system can function not only as a sampler/collector but also as an analytical method. The COBRA system offers a way to rapidly sample and minimize analysis requirements by using an array that varies by both pore size and chemical functionalization within a given pore. This design allows for not only interaction with extremely diverse chemical species, but also the reduction or elimination of traditional gas chromatography which is used for chemical separation before analysis by mass spectrometry. The COBRA system consists of separate collection and desorption mechanisms. The collection portion of the COBRA unit weighs less than 1 kg.

The COBRA system offers a way to rapidly sample and minimize analysis requirements by using an array base that varies by both pore size and chemical functionalization within a given pore. This design allows for not only interaction with the most diverse chemical species, but also the reduction or elimination of traditional gas chromatography of used for chemical separation before analysis by mass spectrometry. It is this core concept of the multi-variate tunability that truly makes CDC unique, for not only can the CDC be an adsorbent method, but also an analytical method. The COBRA systems thus provides a high accuracy/fidelity sensing system that greatly reduces analysis time by minimizing or even completely eliminating the GC component of GC/MS, thus removing the rate limiting step of gas chromatography and allowing for rapid analysis in quantity per instrument through direct MS injection. The millisecond desorption by inductive or microwave heating coupled to the COBRA array concept can lead to direct MS analyte injection per CDC variant; thus removing the rate limiting step of gas chromatography and allowing rapid analysis in quantity. COBRA combines by rapid adsorption/desorption, integrated analytical capability, and a sleek, streamlined low weight design.

The COBRA unit utilizes a coupon with multiple sorbent containers that provide flexibility for analysis. The sampling coupons are stored in an indexable container. As shown in FIG. 1, up to 100 sampling coupons are stored in an indexable carousel that is indexed by a stepper motor to bring each sampling coupon into the sampling chamber one at a time, similar to a 35 mm slide projector. Although a circular carousel is shown, the sampling coupons also can be contained in an indexable straight carousel. Once sampling is complete, the exposed coupon is returned to the carousel where it is stored for subsequent analysis and is replaced by the next coupon from the carousel. Air sampling pumps, motor controllers and electronics are mounted in the cylindrical space in the center of the coupon carousel. The samples are time and GPS stamped to generate desired chemical mapping data.

Figure 2:
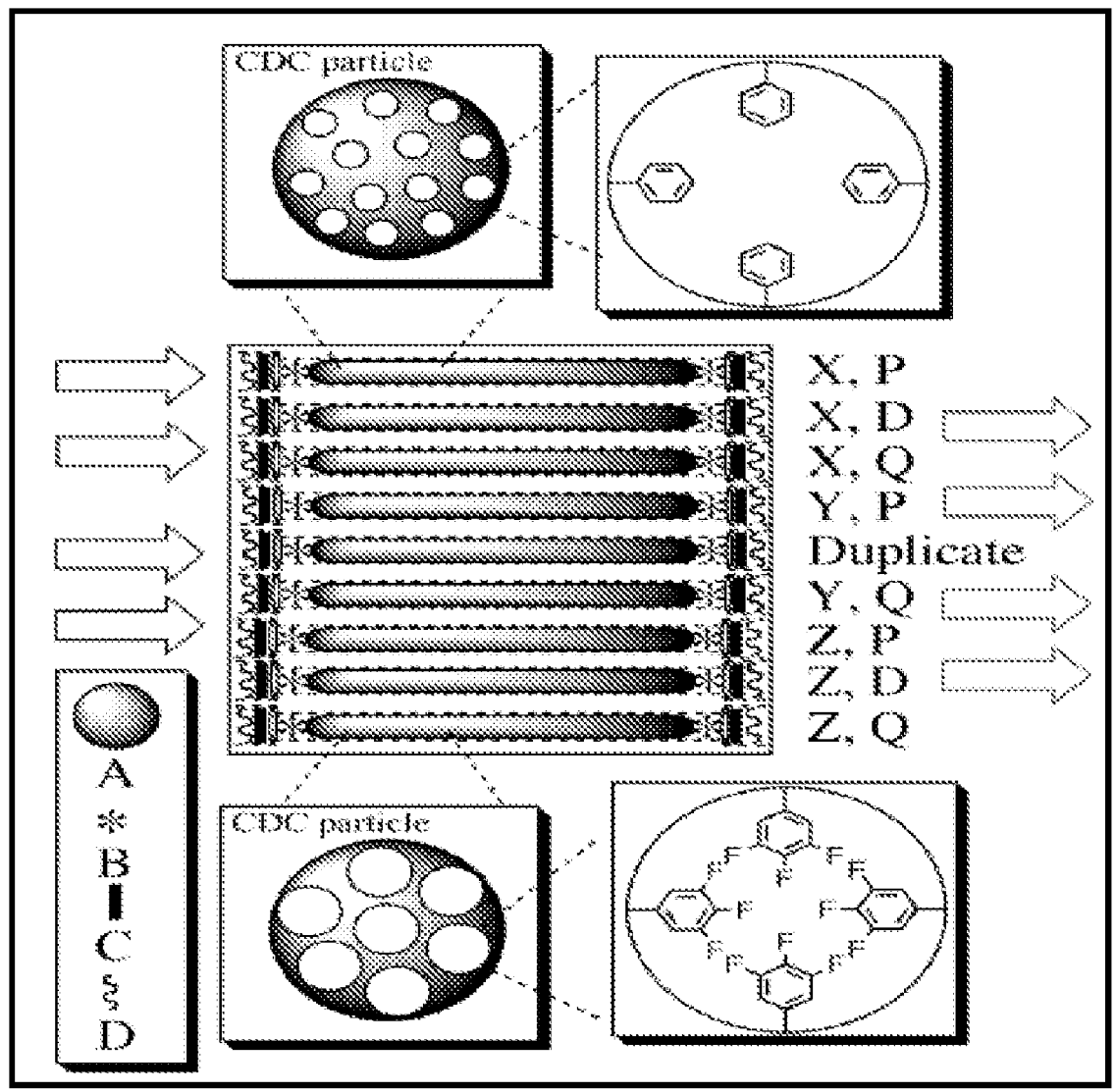
FIG. 2 is a diagram of the COBRA system which shows simultaneous sampling by many modified CDC materials

The hybrid adsorbent-analyte of COBRA is arrayed within a sampling coupon such that many modified CDC materials are exposed simultaneously for atmospheric sampling as shown in FIG. 2. The sampling coupon may include various numbers of different unique CDC variants which are individually addressable, typically from 1 to 12, e.g., 2, 4, 6, 8, 10 or 12. The sampling coupon additionally may include a sector which contains a mixture of all the other CDC variants on the sampling coupon.

In one embodiment, a nine sector array (XYZ-PDQ) is used. Optimum weighting of the granularity is experimentally determined. One sector is reserved for a mixture of all the CDC variants displayed on the coupon in order to provide an internal duplicate to mitigate against malfunction, anomalous results, or loss of chain of custody. Although, the entire coupon is heated via infrared radiation to provide flash thermal desorption, each individually compartmentalized CDC variant can be individually accessed. With proper timing, each CDC variant is tapped for analysis only after adsorbent release, and thus each CDC acts as its own concentrator. Provision of a mass spectrometer per CDC variant, e.g., a MS array as per the samples within the coupon, provides real time analysis limited only by the adsorbent release rate and allows for a chemo-informatics library approach to analysis.

Each CDC variant is unique and identifies one particular class or functionality of a chemical, e.g., aromatic, acid, base, etc. Since each specific chemical has a CDC array "fingerprint," a given result can be matched against a library. For example, a mass peak of 182 amu only specifies an empirical formula of $C_7H_6O_4N_2$, while the array specifies chemical interaction with CDC variants "2," "3," and "7" and thus identifies a 182 amu peak as dinitrotoluene. With a nine-sector array, all or virtually all chemicals can be identified with specificity.

Of particular note is the ability of COBRA to greatly minimize or eliminate over saturation of the entire sampling device by a single environmental contaminant. For example, a deluge of JP8 from a passing vehicle during a GPS waypoint sampling will only affect the CDC variants within the coupon targeted towards hydrocarbons of a particular size. A variant targeted towards another interaction, e.g., a base, is unaffected. This is in distinct contrast to traditional "catch all" adsorbents like those produced by Tenax®. In addition, "channel" analysis allows each MS to be windowed to the analyte mass of specific interest, so that any substance outside the window is ignored analytically.

In an alternative embodiment, the COBRA adsorption coupon includes a stacked bed of sorbents to increase the number of gases the COBRA unit can capture and desorb.

In operation, the COBRA system is loaded with a carousel of sample coupons that are loaded with CDC for collecting the targeted chemical vapors. Sampling is performed for a programmed time of less than 5 minutes before the exposed coupon is swapped for an unexposed coupon and returned to the carousel together with a recording of the time/position data of the sampling event. In the analysis phase a carousel of exposed coupons together with the recorded data is delivered to the analysis mechanism. Each coupon is rotated in turn into the analysis mechanism where the sample tubes are individually exposed to individual GC/MS analyzers and to an individual inert carrier gas supply.

The desorption mechanism heats the sample material rapidly and after reaching the proper temperature, the eluted samples are carried into the GC/MS array. After analysis, the coupon is removed from the analysis mechanism to be replaced by the next coupon. Repetition of this process provides the analysis of all sample tubes in all coupons and the storage of the analysis data together with the time/position data for each coupon.

The analyte is desorbed from the cartridge via infrared (IR) heating under a carrier gas flow. The heat is provided by a pair of IR emitters which are tuned to match the absorption profile of the CDC material. The material is heated to around 240° C. under flowing helium and is collected in an external cryo-focuser to be transferred to the analysis equipment, e.g., a gas chromatograph. A preferred desorption flow is approximately 300 mL/min.

Identification of the material follows its desorption and generation of its mass spectrum entail comparisons of the materials fingerprint against a mass spectrometry library. There are many available mass spectrometry libraries that can be used, and these can be supplemented with experimental data relating to materials not contained in any library. A computer with search algorithms aids in analyte identification.

A somewhat more complicated, yet equally effective method, entails the use of surface wetting chemistry for analytes that are particularly difficult to identify. The use of surface wetting chemistry increases the selectivity towards a given analyte. A combination of these approaches can provide 95% accuracy for an adsorbent sample mass of less than 0.5 grams.

Hyperadsorbent Material

The adsorbent material according to the invention is CDC that has a unique and broadly tunable pore size advantage. The ability to tune the pore size to exactly fit a molecule of interest is of primary importance for gas separation. CDC offers a wide range of pore sizes and can be tuned with a sub-nanometer precision, 5 Å, which is not possible in other materials. Tunable pore size and narrow distribution are key to proper selectivity when sampling diverse of gas species and in controlling the adsorption and desorption processes.

Figure 3:
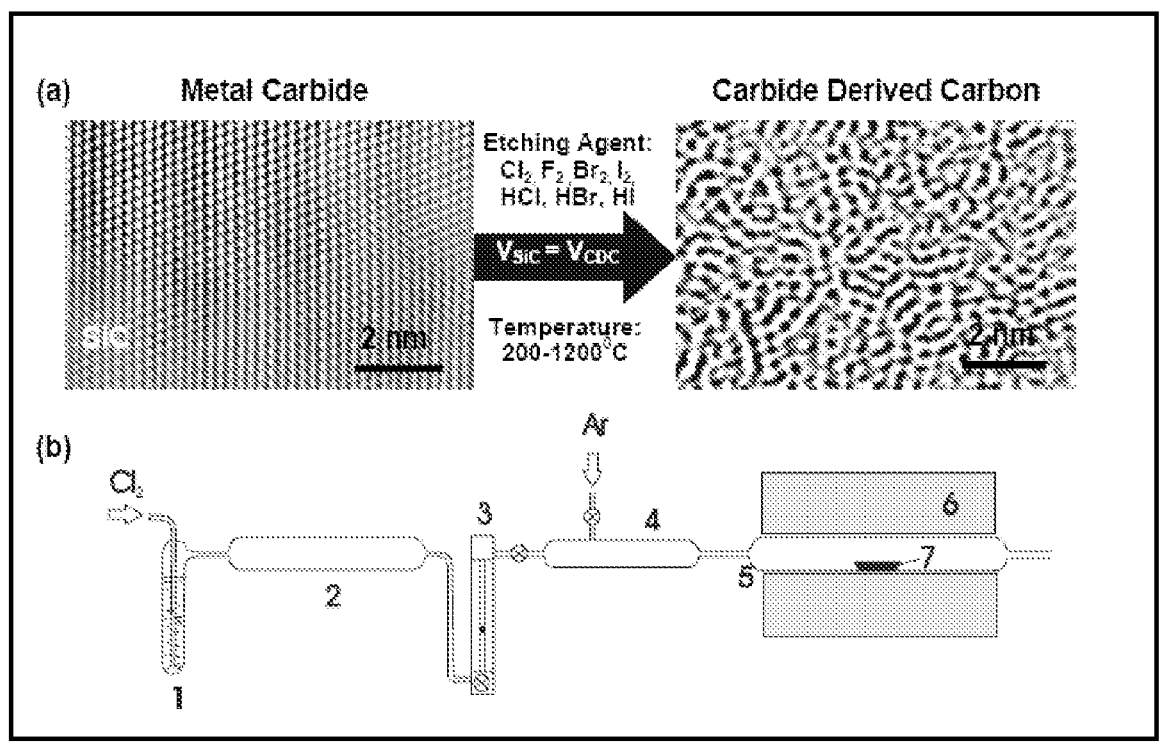
FIG. 3 shows manufacture of CDC by leaching metals from a carbide ceramic in a high temperature halogen environment.

CDC is formed by leaching metals from a carbide ceramic in a high temperature halogen environment, as shown in FIG. 3. The metal carbide process is shown in (a). The chlorination apparatus is shown in (b), and includes sulfuric acid 1, desiccant 2, flow-meter 3, mixing column 4, fused silica reaction tube 5, tube furnace 6 and boat 7 with initial raw carbide. Prior to demetallization, solid metal carbides are milled to produce any desired particle size, a preferred size being on the order of 0.5 mm (30-40 mesh).

Figure 4:
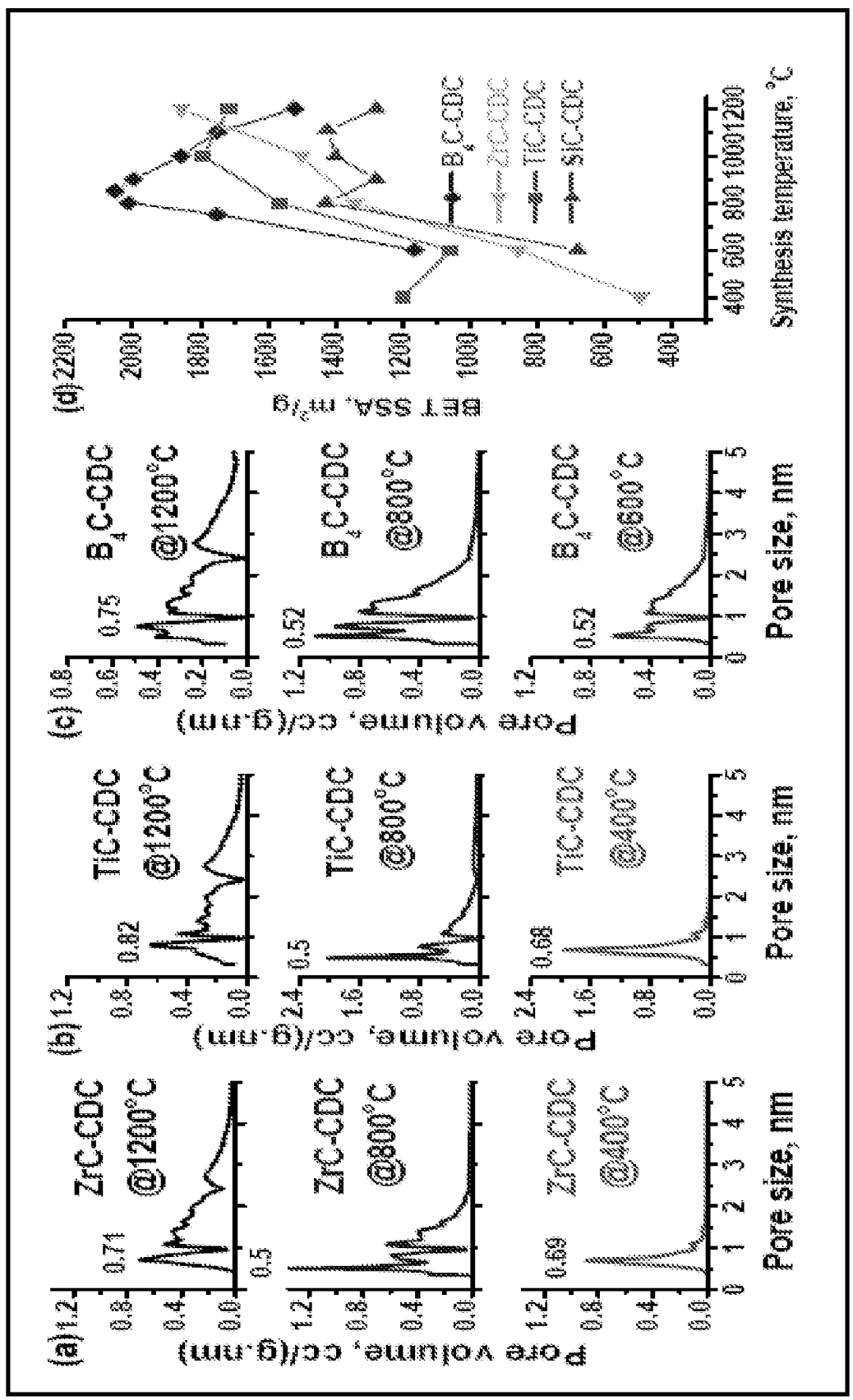
FIG. 4 are plots of pore size as a function of starting metal carbides and processing conditions.
Figure 5:
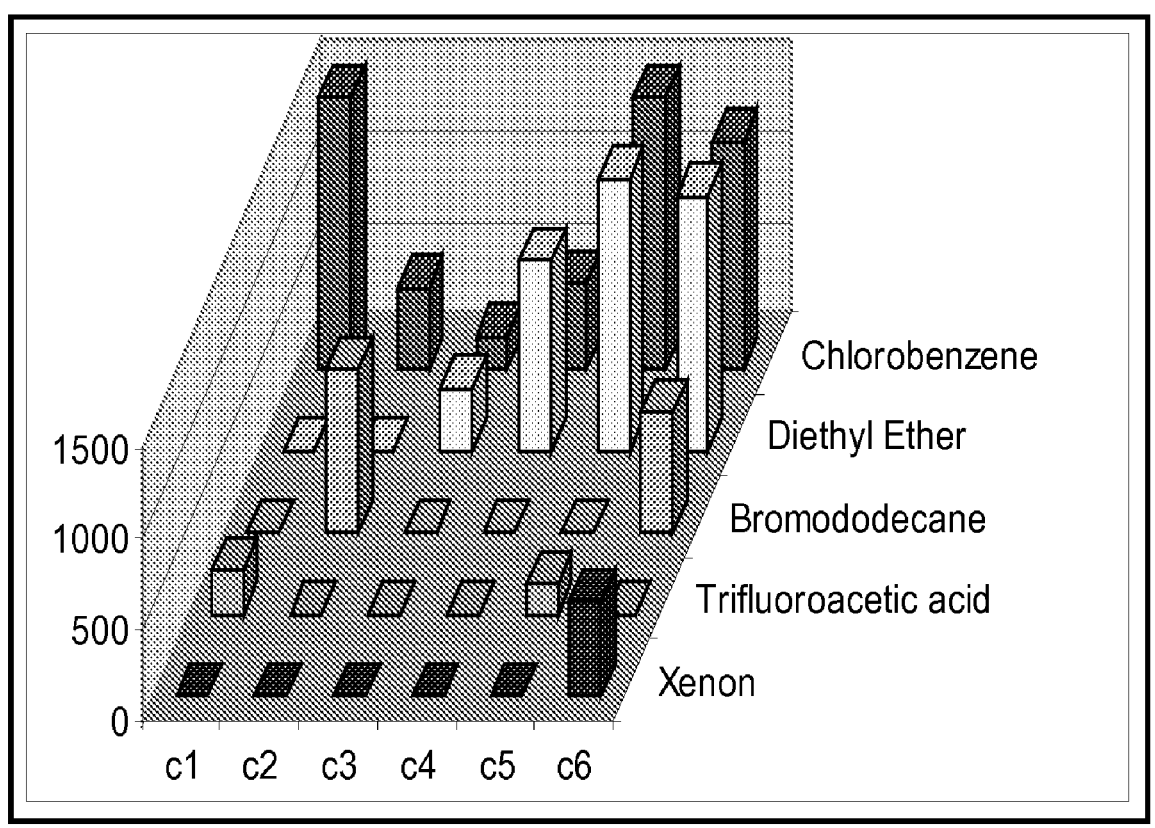
FIG. 5 illustrates an array with selective adsorption of analytes to CDC with varying pore size and surface treatment.

Pore size is controlled by the composition and structure of initial carbide, chlorination temperature (300-1300° C.), make-up gas composition and other processing variables, as shown in FIG. 4. The resultant material is nanoporous carbon that has sub-nanometer tunable pore size (0.6 nm to 3 nm) with a narrow pore size distribution by choice of starting carbide and post processing temperature. Yushin, *Carbon* 2005, 43, 2075-2082. This material control allows selective binding of gas species including xenon, as shown in FIG. 5. This enables control of adsorption and desorption processes and minimizes cross reactivity between analyte species. CDC has extremely high surface areas (300 to 2300 $m^2/g$) and large pore volumes (up to 1 $cm^3/g$), enabling maximum gas adsorption capacity. Gogotsi, *Nature Materials* 2003, 2, 591-594. High adsorption capacity has been shown for hydrogen, methane, and ethane (up to 5× better than competitive technologies). Yushin, *Advanced Functional Materials* 2006, 16, 2288-2293.

In one embodiment, metal carbides are placed onto a quartz sample holder and loaded into the hot zone of an Ar purged horizontal quartz tube furnace. After the desired temperature is achieved, the Ar flow is replaced by 99.5% $Cl_2$ gas for 3 hours at a rate of 10 sccm. After the chlorination treatment, the samples are cooled under Ar flow to remove residual metal chlorides. Residual chlorine is removed using a post-synthesis treatment of 5% hydrogen gas at 600° C. for 2 hours at an approximate flow rate of 2.2 $cm^3$/sec. The final CDC particles are heated and sealed under vacuum. The porous texture of the CDC samples is determined using a Quadrasorb (Quantachrome Instruments, USA) in nitrogen at 77K and carbon dioxide at 273K. The specific surface area is calculated from the Bruauner Elmett Teller (BET) method from $N_2$ sorption. The pore size distribution and pore volume of pores larger than 1.5 nm are determined using the Non Linear Density Functional Theory (NLDFT). The micropore surface area and volume of pores lower than 1.5 nm and 1 nm are determined using the Density Functional Theory in $CO_2$.

CDC can be produced from a wide variety of metal carbides. The choice of metal in the starting material and the conditions used to remove the metal from the carbide together can be used to fine-tune the pore size of the CDC. The resulting material is highly ordered and structured. Exemplary metal carbides include molybdenum-CDC (Mo-CDC) and titanium-CDC (Ti-CDC). The sorption capabilities of each of these differ according to the pore structure for each. Although both showed relatively broad sorption capabilities, Ti-CDC was shown to have less fidelity with larger analytes than Mo-CDC.

CDCs have extremely high surface areas. A typical CDC Brunauer Emmett and Teller Specific Surface Area (BET SSA) measurement is on the order of 1650 m$^2$/g, and may be as great as 2500 m$^2$/g. In contrast, Tenax® TA is a widely used commercial sorbent that has a BET SSA of 35 m$^2$/g. Although surface area alone does not indicate adsorptive capabilities, it does indicate the potential for a material to adsorb.

CDC is produced in a batch process. Tube ovens can be used for fabrication. These are robust and relatively simple equipment so that little down time is required for maintenance. Alternatively, a continuous flow process can be used. CDC is inexpensive to produce, COBRA coupons can be produced for as little as $0.01. In addition, the CDC material can be reclaimed and recycled to be used many times without degradation of performance.

Many CDC materials were tested, and Table 1 gives an accounting of the types of a variety of CDCs that can be used as a hyperadsorbent material. The starting metal carbide, demetallization temperature and surface treatment all have an effect on the pore size, BET surface area and pore volume of the resulting CDC. Six different metal carbides were used as starting material to produce CDC for adsorbent testing. Further variation in those CDCs were produced and investigated by changing the temperature at which each carbide was stripped of metal, with higher demetallization temperatures yielding larger surface areas and pore volumes.

TABLE 1

CDC materials.

| Metal Carbide starting material | Demetallization Temperature, ° C. | Pore Size, nm | Particle Size, μm | BET Surface Area, m$^2$/g | Pore Volume, cm$^3$/g | Surface Treatment |
|---|---|---|---|---|---|---|
| TiC | 600 | 0.67 | 2 | 1058 | 0.47 | None |
| TiC | 800 | 0.67 | 2 | 1566 | 0.82 | None |
| Ti$_3$SiC$_2$ | 600 | 0.5-2.0 | 44 | 1750 | 0.73 | H$_2$ @ 600° C. |
| TiC | 600 | 0.74 | 2 | 1269 | 0.6 | H$_2$ @ 600° C. |
| TiC | 800 | 0.81 | 2 | 1595 | 0.79 | H$_2$ @ 600° C. |
| TiC | 800 | 0.81 | 2 | 1595 | 0.89 | NH$_3$ @ 600° C. |
| TiC | 1000 | 1.1 to 1.2 | 2 | n/m | n/m | Ar |
| TiC | 1000 | 1.1 to 1.2 | 2 | n/m | n/m | Ar + Oxidation |
| TiC | 1300 | 1.5 to 2 | 2 | n/m | n/m | Ar |
| Ti$_2$AlC | 700 | broad | 44 | 1750 | n/m | H$_2$ @ 600° C. |
| Ti$_2$AlC | 600 | broad | 44 | 1850 | 0.825 | H$_2$ @ 600° C. |
| Ti$_2$AlC | 900 | broad | 44 | 1080 | 0.49 | H$_2$ @ 600° C. |
| SiCN | 1000 | 4.9 | 44 | 1519 | 2.2 | H$_2$ @ 600° C. |
| SiCN | 1200 | 5.2 | 44 | 1714 | 2.3 | H$_2$ @ 600° C. |
| Ti$_3$SiC2 | 600 | broad | 44 | 1750 | 0.73 | H$_2$ @ 600° C. |
| Ti$_3$SiC2 | 600 | broad | 44 | 1750 | 0.73 | H$_2$ @ 600° C. |
| Mo$_2$C | 800 | broad | 44 | 2158 | 1.68 | H$_2$ @ 600° C. |
| Mo$_2$C | 800 | broad | 44 | n/m | n/m | Annealed under vacuum @1200° C. |
| Mo$_2$C | 800 | broad | 44 | n/m | n/m | H$_2$ @ 800° C. |
| Mo$_2$C | 800 | n/m | 250 | n/m | n/m | H$_2$ @ 600° C. |
| TiC | 800 | n/m | 250 | n/m | n/m | H$_2$ @ 600° C. |
| Ti$_3$SiC$_2$ | 800 | ~0.4-3.0 | −325 (44) | n/m | n/m | H$_2$ @ 800° C. |
| Mo$_2$C | 800 | n/m | −325 (44) | n/m | n/m | H$_2$ @ 600° C., Vacuum @ 1000° C. |
| Mo$_2$C | 800 | n/m | 300-355 | n/m | n/m | H$_2$ @ 600° C. |
| TiC | 600 | 0.74 | 100-500 | 1269 | 0.6 | H$_2$ @ 600° C. |
| TiC | 800 | 0.81 | >250 | 1595 | 0.79 | H$_2$ @ 600° C. |
| TiC | 600 | 0.74 | 100-500 | 1269 | 0.6 | H$_2$ @ 600° C. |
| TiC | 600 | n/m | 100-500 | n/m | n/m | H$_2$ @ 600° C., Vacuum @ 1000° C. |
| TiC | 800 | n/m | 2 | n/m | n/m | Fluorinated + H$_2$ |
| TiC | 800 | n/m | 250-315 | n/m | n/m | H$_2$ @ 600° C. |
| TiC | 800 | n/m | 250-315 | n/m | n/m | H$_2$ @ 600° C., Vacuum @ 1000° C. |
| Mo2C | 800 | n/m | 300-355 | n/m | n/m | H$_2$ @ 600° C., Vacuum @ 1000° C. |
| TiC | 800 | n/m | 250-315 | n/m | n/m | H$_2$ @ 600° C., Vacuum @ 1000° C. |
| TiC | 800 | n/m | 250-315 | n/m | n/m | H$_2$ @ 600° C., Vacuum @ 1000° C. | n/m = not measured

Different surface treatments also were investigated. The pore surface can be uniquely functionalized without changing the CDC pore size. This allows selective adsorption of gas species and minimizes atmospheric species interactions, e.g., water. Chemical modification via carbon-carbon bond formation can be accomplished through one step gas treatments, electrochemical reduction of diazonium salts or multi-step carboxylate amidations. Surface modification with simple species, such as ammonia, significantly reduced the adsorption of water vapor (0.7% mass increase @90% relative humidity).

With all variables, the sorbent was tuned to allow the broadest adsorption over chemical classes, minimize reactivity on the carbon surface, increase hydrophobicity, and maintain reproducibility batch-to-batch. For each CDC, a battery of tests was used to determine these characteristics. The tests identified four preferred CDCs. Of the four CDCs, two were derived from a titanium carbide (TiC) starting material and two were derived from a molybdenum carbide (Mo$_2$C). All were demetallized at 800° C. and given a subsequent hydrogen treatment at 600° C. The final step for one of each of the two different CDCs was a vacuum anneal at 1000° C. Each of these CDCs performed especially well as broad adsorbers even in humid conditions and was highly reproducible from batch to batch. The tests revealed that the CDCs that only were given the hydrogen treatment without a subsequent vacuum anneal tended to hydrogenate unsaturated hydrocarbons at least partially.

In comparing CDC produced from the two different starting materials, TiC and Mo$_2$C, it was noted that although CDC produced from both materials showed high fidelity, Ti-CDC had slightly lower fidelity than Mo-CDC. Additionally, from a mechanical standpoint, Ti-CDC was less stable than Mo-CDC, having a tendency to disintegrate and physically clog filters. On the basis of these findings, CDC prepared from Mo$_2$C is the most preferred material.

Another criterion that was determined was particle size of the CDC. The first experiments were performed with samples that had 2 micron particles. Sample flow rate is related to particle diameter. For example, the adsorption flow rate needed to sample 100 L of gas in 5 minutes cannot be achieved in a flow bed with 2 micron diameter particles. For a flow rate of 100 L of gas in 5 minutes, a particle size on the order of 100 s of microns was determined to be necessary, particularly given packaging constraints. A preferred particle size is 300-350 micron.

In order to achieve 85% fidelity and accuracy, it is preferable to use one CDC that adsorbs very broadly. A preferred CDC which was determined to have broad sorption capability while retaining hydrophobicity and minimizing surface reactivity was molybdenum carbide-derived carbon that was demetallized at 800® C., subsequently treated with hydrogen gas at 600° C. and then vacuum annealed at 1000° C. Approximately 90 mg of this adsorbent material is in each of the three tubes in our COBRA coupon.

Hyperadsorbent Material Performance
Testing Methods

An adsorption flow bench was used in all testing to characterize hyperadsorbent CDCs. The flow bench delivered sample gases through flow controllers that are interchangeable in the system. Flow rates ranged from 0.1 mL/min to 20 L/minute of dry air, and sample gases of any concentration, or humidified air (through the use of a bubbler) were delivered. The flow bench had a dew point meter, pressure transducer and a flow meter downstream of all flow controllers so that a total flow rate and relative humidity were easily determined. Gas samples in pressurized cylinders were introduced to cartridges of CDC. In order to be able to introduce more exotic challenge gases, a Kin-Tek permeation tube oven was used. The oven had two oven modules, each of which holds up to 8 permeation tubes at two separate temperatures, for a total of 16 tubes in a given experiment. The ovens were plumbed serially with each other and a module which is a secondary dilution chamber. All the components in both figures were plumbed together, giving more opportunities to create gas mixtures of variable concentration.

Example 1

CDC Adsorption

To demonstrate the potential selectivity of this material, analytes from several chemical classes were exposed to CDC materials (synthesized from TiC at 600-1300° C. or MoC at 800° C.) with average pore sizes ranging from 0.7-1.5 nm. The CDC materials had one of four surface treatments (hydrogen; ammonia; argon; and argon with oxidation). Prior to exposure, 70±0.5 mg of each CDC material was placed into a 1 dram vial and sealed in an 11 dram vial with a resealable PTFE septum pierced by a 20 gauge needle. The samples were placed in a glass chamber and heated under vacuum (−165° C. at 5.5×10$^{-5}$ torr) for 24 hours. The chamber was then cooled to room temperature. 10 μL of a solution containing ~2.5×10$^{-5}$ moles of each chemical (except for Xenon which was directly bubbled into the chemical solution) was injected into the chamber and allowed to vaporize and reach equilibrium. After 2 hours, the chamber was evacuated (1×10$^{-4}$ torr) at room temperature, backfilled with nitrogen, and opened. The needles were quickly removed to produce a sealed sample with negligible atmospheric contamination and allowed to sit for three days. Ten μL of the gas head-space above the CDC were directly injected into the GC/MS before and after heating the samples at 240° C. to induce desorption. The injection, prior to heating, indicates that all species detected were desorbed from the material. FIG. 5 illustrates the selectivity of the minimally functionalized CDC materials. Depending on pore size and functionality, the total amount of adsorbent detected by GC/MS changes.

Example 2

CDC Adsorption of Weakly Adsorbent Species Compared to Commercial Sorbents

The hyperadsorptive capabilities of various CDCs were tested against several commercial sorbents. Absorption of low molecular weight, high vapor pressure analytes (ethane, propane, xenon) known to be weakly adsorbent was tested.

Figure 6:
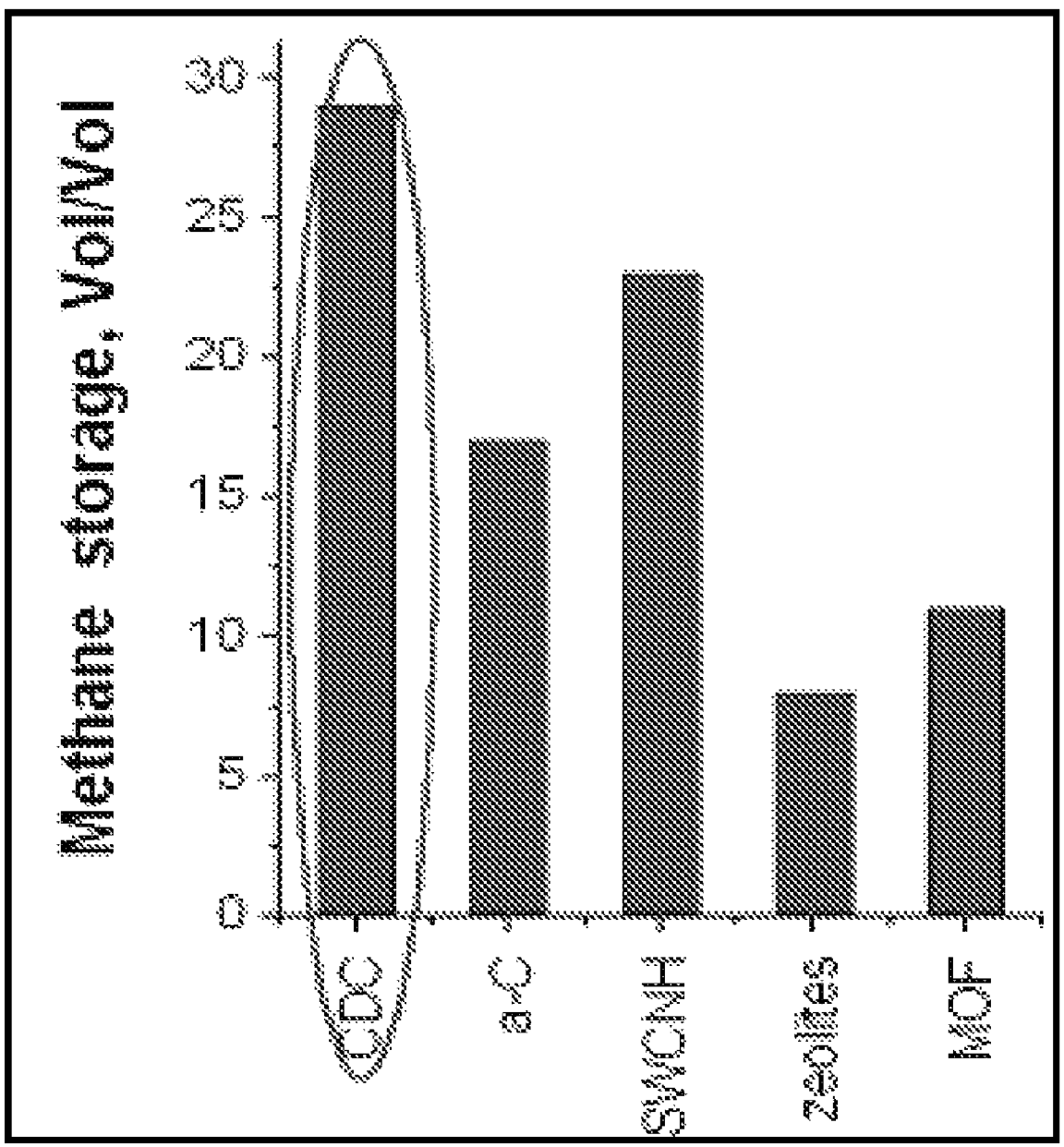
FIG. 6 shows methane storage of CDC at room temperature and atmospheric pressure versus other adsorbents.

CDCs demonstrated superior storage capacity for methane uptake at ambient pressure as compared to zeolites, MOFs, and carbon nanotubes. As shown in FIG. 6, experiments on selected CDC samples showed that CDC outperformed activated carbons, MOFs, zeolites, and SWCNTs for methane uptake. This is attributable to the pore size distribution and tunable size of the pores and also to the strength of the interaction between the CDC materials and the gas molecules. This is evident by the very large heat of H$_2$ adsorption on CDC, 8 kJ/mole, as compared to MOF and SWCNT.

Further experiments were carried out for ethane. Ethane is difficult to adsorb, as it is a small molecule with a high vapor pressure and no chemical functional groups. CDC with an average pore size of 0.8 nm derived from TiC was used. This adsorbent has a much larger adsorption capacity than other adsorbents. CDC was compared to electro-spun activated carbon nanofiber (AcNF), activated carbon fiber cloth (ACFC) made from a phenolic resin, or Kynol® ACFC-activated, Calgon BPL®, a high-experiments on selected CDC samples showed that CDC outperformed activated carbons, MOFs, zeolites, and SWCNTs for methane uptake. This is attributable to the pore size distribution and tunable size of the pores and also to the strength of the interaction between the CDC materials and the gas molecules.

Ethane and water adsorption isotherms for ammonia passivated CDC (TiC synthesized at 800° C. with average pore diameter 0.8 nm) were measured using a gravimetric sorption analyzer. From the observed ethane isotherm, an adsorption rate of 33.8 (mg ethane/min)/g CDC was calculated. After 5 minutes a total of 150 mg of ethane were adsorbed. Thus, in a 100 L air sample, all of the ethane can be adsorbed if its concentration is ~0.1% of the total air sample. This demonstrates that the material has the sufficient capacity that saturation from exposure to 1% gas mixtures during the sampling process is unlikely. Additionally, water adsorption isotherms showed that the minimally functionalized CDC material also has the ability to exclude water as indicated by the less than 1% mass change in a 90% relative humidity atmosphere. Thus, with proper functionalization of the CDC, water adsorption can be greatly diminished.

Figure 7:
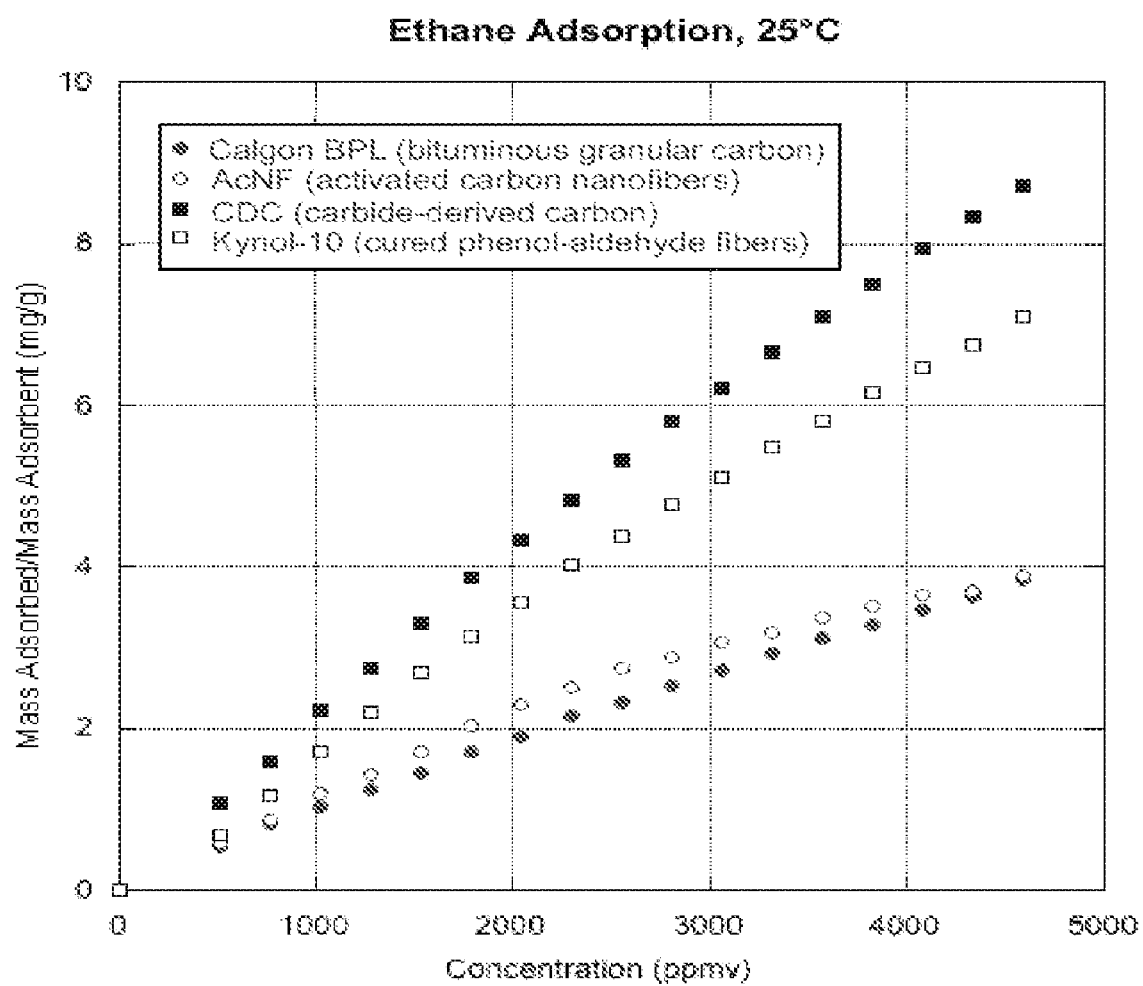
FIG. 7 shows ethane adsorption at room temperature for CDC and several high performance commercial sorbent materials.

The uptake of ethane, measured in mg of adsorbate/g of adsorbent, was graphed as a function of concentration of ethane in the gas phase at 25° C. above the adsorbate with each measurement being taken at equilibrium. A typical result is shown in FIG. 7. CDC was compared to bituminous-coal-based BPL® from Calgon Corporation, activated carbon nanofibers (AcNF), and Kynol®-10. The amount of ethane that the CDC was capable of adsorbing as opposed to the high performance commercial sorbents was striking. These results are indicative of high adsorption capacity, and subsequent testing confirmed these results. Each COBRA coupon required only 270 mg of material per coupon.

Example 3

Exclusion of Water

Figure 8:
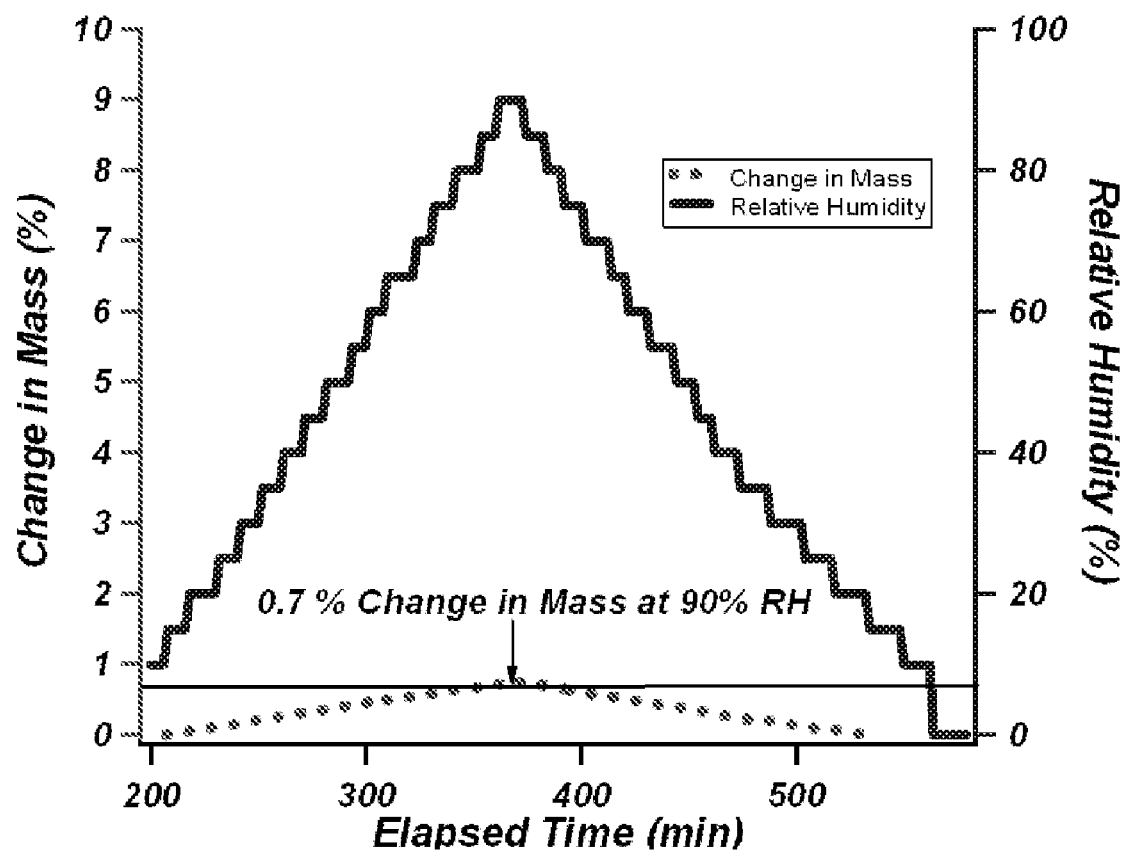
FIG. 8 shows the change in mass of CDC at equilibrium in the presence of increasing and decreasing relative humidity.

CDCs were tested to determine hydrophobicity as any hyper-adsorbent material that can be successfully used for air sampling must exclude as much water vapor as possible. A measure of the hydrophobicity of CDC was determined in both equilibrium and dynamic experiments. FIG. 8 shows the uptake of water on a CDC sample reported in percent change in mass as a function of time during an increase in relative humidity. At 90% relative humidity, only 0.7% change in the mass of CDC occurs at equilibrium. Calculations have shown that over 50% of the pore volume of the CDC is still available even at relative humidity greater than 80%. This extreme hydrophobicity allows CDC to be used in high humidity environments.

In order for a highly hydrophobic material to function successfully in COBRA, it must remain adsorbent for analytes of interest while still excluding water. To confirm that a hydrophobic CDC has this ability, a series of experiments were completed with 25 analytes being exposed to CDC in increasing relative humidity. Analytes that were adsorbed onto CDC in the presence of increasing relative humidity were subsequently desorbed. The desorption products were graphed as a function of relative humidity. In general, most analytes showed a sharp decrease in desorption with increasing humidity, then continued to decrease only gradually or level off. This was attributed to solvation of the analytes by water in the gas phase, such that analytes did not adsorb as readily on the hydrophobic surface. However, the effect did not appear to impact detection fidelity significantly. For even the most polar compound in the mixture (acetone), there was only a 40% decrease of desorption of acetone from the dry air experiment to 83% relative humidity. The single exception observed was p-ethyltoluene, which showed a slight increase in moles desorbed, a possible artifact of the small quantities of analyte detected.

Example 4

Batch-to-Batch Performance

Batch-to-batch reproducibility was measured to ensure consistency in the adsorption performance and CDC production methods. This was an important performance characteristic to measure prior to combining batches of the same type of CDC, and is a particularly important parameter for scale up of production. Most compounds showed less than 10% standard deviation over the batches.

Adsorption Kinetics and Flow Properties

Kinetics

Adsorption kinetics were measured to gain an understanding of the capabilities of the adsorbent materials. Breakthrough curves from inverse gas chromatographic (IGC) measurements were established for several compounds. These curves were in turn used in part to corroborate the results of the mass transfer coefficient determination from the magnetic suspension microbalance and for the adsorption modeling.

1. Inverse Gas Chromatography Measurements

Inverse gas chromatography was used to measure adsorption kinetics for several gases on the CDC materials. Data was collected for ethane, propane, diethyl ether, nitrogen dioxide, and methyl isobutyl ketone. Of those compounds, data was collected data in the Henry's Law region for propane, diethyl ether and methyl isobutyl ketone. These were used to extract the thermodynamic and kinetic parameters necessary to build relevant computational models.

2. Mass Transfer Coefficients

Overall mass transfer coefficients were calculated using experimental data. Each experiment measured the percent weight change of the CDC at equilibrium. Measurements were performed gravimetrically at several concentrations to obtain an average for the mass transfer coefficient for the CDC. The coefficient was used in an adsorption model.

Material kinetic measurements for the preferred Mo-CDC according to the invention were compared with Calgon BPL® as a standard commercial sorbent reference material and activated carbon beads of the same particle size. The mass transfer coefficient for the material according to the invention was higher than those measured for these other high performance adsorbents, meaning that the Mo-CDC is able successfully to adsorb analytes in short sampling times (5 minutes) and high flow rates (20 L/min).

3. Model of Break-Through Kinetics

A finite-element analysis computer model was developed using the commercial software Comsol Multiphysics™ to simulate the adsorption kinetics of the CDC. A linear driving force assumption, with the boundary conditions shown in Table 2, was used.

TABLE 2

Boundary conditions used in the breakthrough model.

| | X = 0 | X = L |
|---|---|---|
| C | Inward flux | Convective flux (null condition) |
| T | Fixed temperature | Convective flux |
| $T_p$ | Thermal insulation | Thermal insulation |
| $T_w$ | Thermal insulation | Thermal insulation |

The following equations were solved using the boundary conditions in Table 2:

$$\frac{\partial c}{\partial t} + u\frac{\partial c}{\partial x} = -\frac{\partial q}{\partial t} \qquad 1$$

$$\frac{\partial q}{\partial t} = k_m A_s (q^* - q) \qquad 2$$

-continued $$\rho_\theta Cp_\theta \frac{\partial T}{\partial t} - k_\theta \frac{\partial^2 T}{\partial x^2} = Q_\theta - \rho_\theta Cp_\theta \frac{\partial T}{\partial x} \qquad 3$$

$$\rho_p Cp_p \frac{\partial T_p}{\partial t} - k_p \frac{\partial^2 T_p}{\partial x^2} = Q_p \qquad 4$$

$$(d_o^2 - d_i^2)\rho_w Cp_w \frac{\partial T_w}{\partial t} - k_w \frac{\partial^2 T_w}{\partial x^2} = Q_w \qquad 5$$

$$Q_\theta = -\frac{1-\eta}{\eta} h_p A_s (T - T_p) - \frac{4h_w}{d_i}(T - T_w) \qquad 6$$

$$Q_p = Q_{ads} \frac{\partial q}{\partial t} + h_p A_s (T - T_p) + \text{Heat} \qquad 7$$

$$Q_w = 4d_i h_w (T - T_w) + 4d_o h_o (T_o - T_w) \qquad 8$$

Definitions of the terms for these equations are given in Table 3:

TABLE 3

Definition of terms in adsorption breakthrough modeling

| | |
|---|---|
| c | Concentration in air |
| q | Concentration adsorbed |
| T | Air temperature |
| $T_p$ | Particle temperature |
| $T_w$ | Wall temperature |
| u | Velocity |
| $A_s$ | Specific particle surface area |
| $k_m$ | Mass transfer rate |
| $q^*$ | Equilibrium concentration |
| $\rho$ | Density |
| $C_p$ | Heat capacity |
| k | Thermal conductivity |
| h | Heat transfer coefficients |
| $d_i$ | Inner diameter |
| $d_o$ | Outer diameter |
| $\eta$ | Void fraction |
| $Q_{ads}$ | Heat of adsorption |
| Heat | Heat input to particles |

The model showed a very good fit to the experimental results, even though it was completely derived from first-principles and no fitting parameters were used. Adjusting the mass transfer coefficient (MTC) by a factor of three brings the profile of the breakthrough curve into agreement with the experimental results. This is not unreasonable, as the method used to measure the MTC in the microbalance had gas flowing around the sample basket in a laminar flow regime. In the reactor, the flow is forced through the adsorbent and is turbulent, so the MTC would be expected to be much higher at these operating conditions. With the MTC adjusted, the model prediction for breakthrough time was within about 10% of the observed value and the breakthrough curve had a similar profile.

Flow Characteristics Versus Mass of CDC

To ensure that the COBRA coupons would be capable of sampling the maximum amount of gas within a specified 5-minute timeframe, pressure drop and flow rate were measured as a function of CDC mass in several sizes of inner diameter tubing. The measured pressure drop and flow rate were plotted as a function of mass of 350 micron particle size Mo-CDC in a ¼" ID PFA tube. The data from all the experiments indicated that a ¼" ID tube size was necessary in order to achieve a flow of 7 liters per minute per tube (>20 liters per minute for three tubes, or >100 liters total in 5 minutes). A larger tube allows the potential use of large quantities of CDC material with minimal pressure drop.

Desorption Properties and Testing

To perform an analysis of the broadest possible spectrum of adsorbed organics by GC/MS, several features are required from the sample introduction system:

The entire sample should be introduced on-column employing as short a path as possible to minimize losses.

The desorption system should have a low dead volume to prevent peak broadening.

The sample introduction system should be cool at the time the sample is inserted Several methods of heating the CDC for desorbing captured analytes can be used. Potential methods for imparting energy into the CDC for heating include microwave, resistance, inductive, and infrared (IR).

Inductive heating is a process where eddy currents are generated within the metal (in our case nickel) and resistance leads to Joule heating. When beyond its Curie point, the induction process becomes less efficient and the nickel temperature reaches equilibrium. The primary advantages of inductive heating are uniformity of heating throughout the sample and fast temperature rise (334° C. in 100's of milliseconds).

Joule heating or resistive heating, is used in nearly all commercial thermal desorption analytical systems which interface to a GC/MS. Typically, a jacket surrounding the sample tubes or tray is heated resistively heating the sampling tubes and desorbing the analytes into a carrier stream. The advantages of this well established method are simplicity and low risk, no added coupon weight.

Microwave heating can also be used to desorb the analytes from the sampling tubes by heating the CDC directly using microwaves directed at the coupon. The advantages include precise uniform and rapid heating while adding no coupon weight.

Infrared heating transfers energy to a body with a lower temperature through electromagnetic radiation. No contact or medium between the two bodies is needed for the energy transfer.

The chief criteria for choice of heating is the speed at which optimal temperature can be reached, since desorption is kinetically favored over decomposition for surface-bound analytes. Testing showed that CDC does not resonantly couple in the range of microwave wavelengths and CDC did not heat. Experiments for testing the CDC by irradiating with microwaves were performed using 100 W at 2.45 GHz and no heating was observed. Additionally, transmission was measured through a 1 mm thick layer of CDC as an obstacle within the waveguide and no resonant feature was observed within the X-band.

Experiments using resistive (or Joule) heating were conducted by pressing a packed column of CDC between electrodes to impart energy onto the CDC. Using a 100 milliamp current, an initial heating rate of ~1° C. per second was the fastest temperature ramps that were achieved with this method. Beyond the slow heating rate, there were also issues with the material arcing if it was not packed tightly enough and the material itself showed variable resistance throughout experimentation.

A method of induction heating also was developed and tested for heating the CDC. In this set-up, a nickel alloy foil was included in the tubing with the CDC. The tube was placed inside a radio frequency (RF) induction coil. Several alloys and RFs were investigated for this type of heating. However, the initial heating rate was still low (~2° C. per second).

Finally, infrared lamps were tested as a means of rapidly heating the CDC. Because the CDC is basically a black body, the infrared lamp can be tuned to overlay in the region that the CDC adsorbs IR with the largest molar absorptivity value. IR heating achieved the desired desorption temperature the most quickly, with an initial temperature ramp rate of approximately 25° C. per second. This method of heating had the fastest initial ramp rate and therefore is the preferred method for heating the CDC for desorption.

Desorption Temperature Studies

A series of experiments were performed to determine the optimal desorption temperature and time. An upper temperature of 260° C. was used in PFA tubes, and an upper temperature in excess of 300° C. was used in glass tubing. For the analyte suite used in the studies, temperatures in excess of 250° C. did not yield great gains in amounts of desorption products, and there was an increased cross reactivity with some of the halocarbons in the testing suite.

The experiments were performed using the IR for desorption. Desorption products were captured in a Tedlar® (DuPont) bag and subsequently injected into the GC/MS. This allowed the temperature experiments to be investigated very readily as a function of time as well. For each of these experiments, a series of Tedlar® bags were used to capture the fractions from each of the first five minutes of the desorption experiment. The desorption products from each minute could then be interrogated separately to get a complete understanding of what percentage of the total gas desorption products come off of the CDC in given time increments of the experiment. The experiments showed that over 85% of the total desorbed species evolve into the gas phase in the first four minutes of the experiment.

Desorption Versus Mass of CDC

The appropriate amount of CDC to use per tube in an experiment was investigated as a function of desorption species. A range of 50-300 mg of CDC for one tube was investigated at an exposure concentration of 100 ppb. As the mass of CDC was increased in the tube, there were diminishing returns at approximately 150 mg, and decreased yields past this mass amount given all other chosen variables. From this set of experiments, it was determined that ~100 mg per tube produced optimal results.

Desorption Flow Rate

The final parameter to determine for the desorption system was the optimal flow rate of the carrier gas to ensure the most desorbed species. Experiments were performed with a He carrier gas flow rate between 100 ml/min and 300 ml/min. Eighteen compounds were desorbed from CDC samples at 100 ml/min and 300 ml/min over a 6 minute period. In both flow rate experiments, the 100 ml/min flow rate proved to be optimal throughout the temporal profile. It is of note that larger species desorb to a greater extent later in the temporal profile. While the result of increased analyte desorption at the smaller flow rate seems counterintuitive, the decreased analyte collection at the higher flow rate may be due to cooling effects since the helium carrier gas was not preheated.

COBRA Packaging and Apparatus

Sample Coupons

Packaging for the sample coupons requires sufficient structural rigidity at the temperatures required for the thermal desorption process. A glass tube remains rigid at operating temperature. The glass tube is sealed with two O-rings (one at each end) which are placed in grooves machined in the caps.

A perfluoroalkoxy (PFA) plastic material, such as medical grade PFA 440 HP tubing, Shore 46D, also can be used. The PFA tubing is solvent washed and dried with dry nitrogen and then is heat sealed within a dedicated dry box. The required mass of CDC variant which has already received a 300° C. cleaning under medium vacuum is placed in the tube. If inductive heating is chosen for the desorption process, a 0.875 by 0.002 inch OD nickel foil, pre-treated with Restek® is inserted prior to addition of the CDC variant. The nickel foil provides minimal mass and is pretreated with a fluoro-siloxane coating to achieve nano-gram adsorbent inertness. This embodiment requires the use of a glandular type seal at the top and bottom of the tube with the valve seal being independent of the seal to the manifold during desorption. This gives the advantage of not only divorcing the sealing mechanisms, but also of removing the axial load from the tube because there is no load required to maintain the seal. The tube is essentially suspended between the two halves of the manifold.

A third alternative is an aluminum coupon. The raw aluminum coupons (38×24×4.5 mm), as machined, receive a solvent wash followed by high temperature oxidation of the surface to provide a thermal isolation layer as well as a scrupulously clean surface. If induction heating is to be employed, the coupon is electrochemically coated with an approximately 0.002 inch nickel coating. The coupons then are coated with Restek® to achieve nano-gram level inertness. The coupons then are loaded with the requisite CDC variants and heated to 250-300° C. under medium vacuum (~$10^{-5}$ torr) for 24 hours. The entire vacuum unit then is transferred to a dedicated dri-box where septa are added and crimp sealing performed. The coupons are then stored under nitrogen until used.

A fourth alternative is polyetheretherketone (PEEK) coupon, which is and accessed for sampling in the manner as the aluminum coupon described above. The major difference between the aluminum and PEEK designs, apart from the material, is that a thin strip (0.875"×0.5"×0.002") of Restek® coated nickel is included in each tube (as in the PFA design), since PEEK is a polymer and cannot be electroplated.

Figure 9:
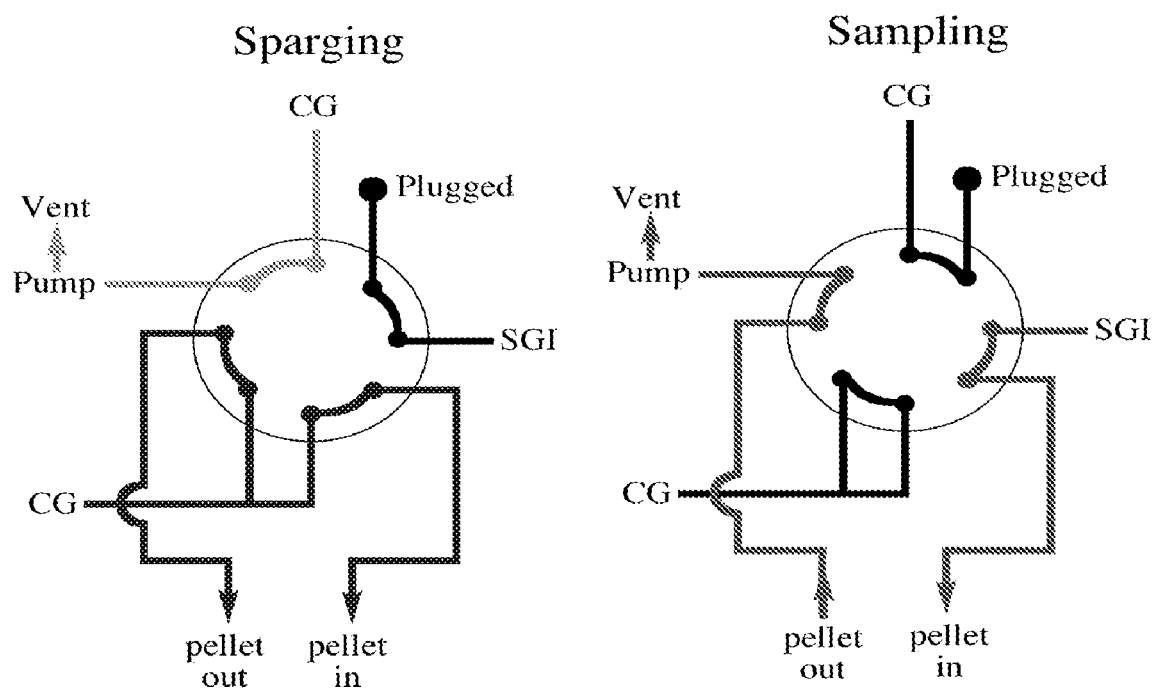
FIG. 9 is a diagram of an eight way GC valve flow pattern for needle sparge and sample access.

Access to the packaged CDC is accomplished via needle penetration of a resealable Teflon lined silicone septa. The interface must accomplish two major tasks: proper needle location and switching between an inert protection gas and the actual sample flow. Monte Carlo calculations show that in order to pull the requisite Phase I volume across the bed, a pressure drop of ~50 mbar must be generated. As the needles are exposed to the atmosphere both before and after interaction with the coupon through the septa, a flow of inert gas through the open needles is required. In addition, inert carrier gas should be provided to the pump while in operation. Therefore an eight-way GC gas control valve can be employed with a custom lever action coupon holder for needle location and penetration. When tripped by a microswitch, the sampler valve change from a sparge configuration to a sample flow loop, as shown in FIG. 9. When sampling is complete lifting of the needle lever arm reverses the flow paths restoring the needle sparge. The lever base can be changed to accommodate any coupon type and can be configured in single or multiple CDC variants per coupon for array access.

Coupon Carousel

Up to 100 sampling coupons are stored in a circular carousel that is indexed around by a stepper motor to bring each sampling coupon into the sampling chamber one at a time similar to a 35 mm slide projector. Once sampling is complete, the exposed coupon is returned to the carousel where it is stored for subsequent analysis and is replaced by the next coupon from the carousel. Air sampling pumps, motor controllers and electronics are mounted in the cylindrical space in the center of the coupon carousel.

In operation, the COBRA system is loaded with a carousel of sample coupons that are loaded with CDC for collecting the targeted chemical vapors. Sampling is performed for a programmed time of ≦5 minutes before the exposed coupon is swapped for an unexposed coupon and returned to the carousel together with a recording of the time/position data of the sampling event.

The sampling mechanism is controlled by a microprocessor which sequences the sampling events, collects and archives the time/position data, and provides a mission design and storage interface. Mechanical articulation is achieved with small stepper motors under computer control. Sampling starts by indexing the carousel to deliver the proper coupon into the sampling mechanism. The hypodermic needles are mounted as an array of nine on an inlet manifold and an array of nine on an outlet manifold. A stepper motor and captive cam Geneva mechanism drives these needle arrays to penetrate the nine inlet and nine outlet septa on the sampling tubes. The air pump then draws the sample air flow through the sample tubes. On completion of a sampling event, the captive cam mechanisms withdraw the hypodermic needles from the coupon allowing the septa to close and to seal the sample tubes from subsequent contamination. The exposed coupon is now replaced in the sampling mechanism and replaced by the next unexposed coupon. The housing design and material provides rapid access to the sampling carousel, environmental protection, light weight, free flow inlet and outlet air path, and attachment to the chosen vehicle.

In the analysis phase a carousel of exposed coupons together with the recorded data is delivered to the analysis mechanism. Each coupon is rotated in turn into the analysis mechanism where the septa of each of the sample tubes is individually penetrated by hypodermic needles connected to individual GC/MS analyzers and to an individual inert carrier gas supply. The desorption mechanism heats the sample material rapidly and after reaching the proper temperature, the eluted samples are carried into the GC/MS array.

After analysis, the needles are withdrawn and the coupon removed from the analysis mechanism to be replaced by the next coupon. Repetition of this process provides the analysis of all sample tubes in all coupons and the storage of the analysis data together with the time/position data for each coupon.

Coupon-Analysis Apparatus Interface

Several criteria must be addressed with any sample package-GC/MS interface. These include the minimum added head space, zero atmospheric contamination, and preferably as little instrument modification as possible to compare analytical results with non-packaged test suites. In addition, the sample coupon must be accessed per the final devices as well as using the ultimate desorption technique.

Figure 10:
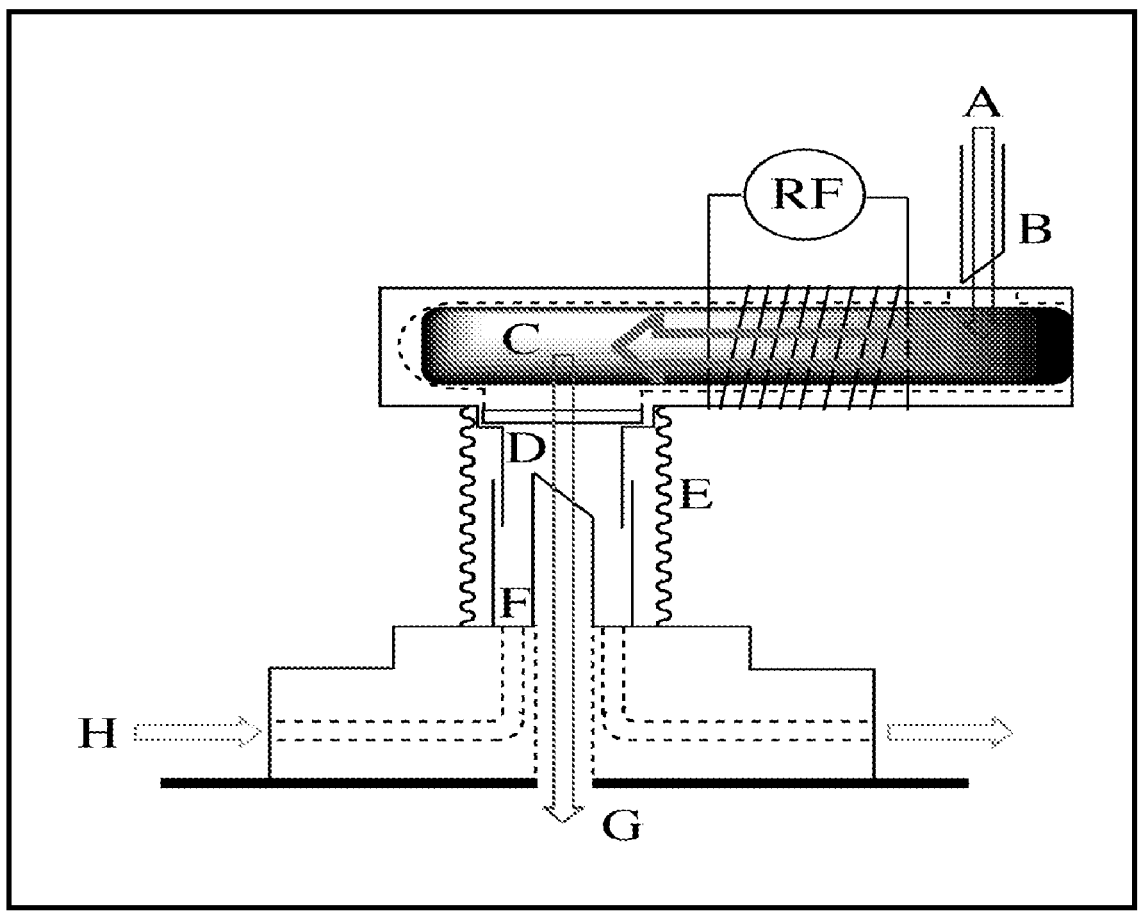
FIG. 10 shows a GC/MS—sample package interface.

A sample interface is shown in FIG. 10 and addresses the requirements listed above. Carrier gas is introduced in one end (A), the sample will then be directly connected, within its packaging (C), to the inlet of the GC instrument thru a modified injection block (G) where the septa (D) has been relocated on a corrugated metal bellows (E) terminated in a conformal package (B) slot with a needle (F) of the required sizing contained within. The sample will then be desorbed by the method of choice, e.g. induction, joule heating, etc. An inert gas purge (H) eliminates possible contamination from the piercing process. Depending on the test suite, the GC can be run in split or splitless mode for MS and FID quantization in addition to a dopant being added to the carrier gas upstream of the sample packing for an internal reference. The GC, an Agilent 6890N, uses a "flip top" quick exchange injection block, switching between the typical injection port and the sample package interface will require zero retooling. A minimal modification from traditional manual injection mode, e.g., the µL headspace addition, allows quantization data to directly correlate to sample packaging data. This allows quantized tracking of changes due to CDC packaging, packing (mesh), carrier flow rates and desorption power parameters.

Thus, a chemically-modified organic CDC-based rapid analysis has been described according to the present invention. Many modifications and variations may be made to the techniques and structures described and illustrated herein without departing from the spirit and scope of the invention. Accordingly, it should be understood that the methods and apparatus described herein are illustrative only and are not limiting upon the scope of the invention.

What is claimed is:

1. An air sampling assembly comprising:
   a plurality of sampling coupons, each sampling coupon comprising a plurality of different carbide-derived carbon (CDC) variants which vary with respect to one or more of pore size, surface chemistry, and surface electrical properties, for adsorbing chemicals in an air sample; and
   an indexable container for holding said plurality of sampling coupons, which allows the sampling coupons to be individually addressed
   wherein a matrix of 8 unique CDC variants and a ninth control comprising all of the 8 unique CDC variants are contained on each sampling coupon.

2. An air sampling assembly according to claim 1, additionally comprising means for indexing the indexable container.

3. An air sampling assembly according to claim 2, wherein the indexing means is a stepper motor.

4. An air sampling assembly according to claim 2, wherein the indexing means additionally comprises means for recording the time and location where the sample was collected.

5. An air sampling assembly according to claim 1, additionally comprising means for desorbing the chemicals which are adsorbed on the sampling coupons.

6. An air sampling assembly according to claim 5, wherein the desorbing means comprises IR heating.

7. An air sampling assembly according to claim 6, additionally comprising means for analyzing the chemicals which have been desorbed from the sampling coupons.

8. An air sampling assembly according to claim 7, wherein the analyzing means comprises a mass spectrometer.

9. An air sampling assembly according to claim 8, wherein the analyzing means additionally comprises a gas chromatograph.

10. An air sampling assembly according to claim 8, additionally comprising means for identifying the chemicals which have been desorbed and analyzed.

11. An air sampling assembly according to claim 10, wherein the identifying means comprises a mass spectrometry library.

12. An air sampling assembly according to claim 1, wherein each of the plurality of CDC variants is unique.

13. An air sampling assembly according to claim 1, wherein each sampling coupon includes different unique CDC variants which are individually addressable.

14. An air sampling assembly according to claim 13, wherein the plurality of different CDC variants vary with respect to pore size and are uniquely functionalized.

15. An air sampling assembly according to claim 1, wherein each sampling coupon includes a stacked bed of sorbents to increase the number of gases the coupon can capture and desorb.

16. An air sampling assembly according to claim 1, wherein CDC variants vary with respect to pore size and also with respect to one or both of surface chemistry and surface electrical properties.

17. An air sampling assembly according to claim 1, wherein the plurality of different CDC variants form an array of CDC materials which contain various pore sizes, surface chemistry, and surface electric properties.

18. A method of air sampling, comprising:
- providing an indexable container containing a plurality of sampling coupons, each sampling coupon comprising a plurality of different carbide-derived carbon (CDC) variants which vary with respect to one or more of pore size, surface chemistry, and surface electrical properties, for adsorbing chemicals in an air sample, the CDC variants on the sampling coupon arranged as a matrix of 8 unique CDC variants and a ninth control comprising all of the 8 unique CDC variants; and
- addressing one sampling coupon and exposing it to the air so that a chemical in the air is adsorbed on the plurality of CDC variants on the sampling coupon.

19. A method of air sampling according to claim 18, additionally comprising desorbing the chemicals which are adsorbed on the sampling coupons.

20. A method according to claim 19, additionally comprising analyzing the chemicals which have been desorbed from the sampling coupons.

21. A method according to claim 20, additionally comprising identifying the chemicals which have been desorbed and analyzed.

22. A method according to claim 21, wherein the identifying comprises chemo-informatics.

23. A method according to claim 18, additionally comprising recording the time and location where the sample was adsorbed.

24. A method of air sampling according to claim 18, wherein orthogonal chemical selection criteria are employed which comprise one or more of molecular shape/size, chemical class, and polarizability.

* * * * *